(12) United States Patent
Kim et al.

(10) Patent No.: US 9,763,908 B2
(45) Date of Patent: Sep. 19, 2017

(54) COMPOSITION CONTAINING MONOACETYLDIGLYCERIDE COMPOUND AS ACTIVE INGREDIENT FOR PREVENTING OR TREATING ATOPIC DERMATITIS

(71) Applicants: ENZYCHEM LIFESCIENCES CORPORATION, Daejeon (KR); KOREA RESEARCH INSTITUTE OF BIOSCIENCE AND BIOTECHNOLOGY, Daejeon (KR)

(72) Inventors: Jae Wha Kim, Daejeon (KR); Sei-Ryang Oh, Daejeon (KR); Kyung Seop Ahn, Daejeon (KR); Ho Bum Kang, Daejeon (KR); Jae Mine Yoo, Daejeon (KR); Tae-Suk Lee, Daejeon (KR); JongKoo Kang, Cheongju-si (KR); Hye Kyung Kim, Seoul (KR); Jin Soo Yook, Daejeon (KR); Yong-Hae Han, Seoul (KR); Ki Young Sohn, Seoul (KR)

(73) Assignees: ENZYCHEM LIFESCIENCES CORPORATION, Yuseong-Gu, Daejeon (KR); KOREA RESEARCH INSTITUTE OF BIONSCIENCE AND BIOTECHNOLOGY, Yuseong-Gu, Daejeon (KR)

( * ) Notice: Subject to any disclaimer, the term of this patent is extended or adjusted under 35 U.S.C. 154(b) by 0 days.

(21) Appl. No.: 14/915,799

(22) PCT Filed: Sep. 3, 2014

(86) PCT No.: PCT/KR2014/008229
§ 371 (c)(1),
(2) Date: Mar. 1, 2016

(87) PCT Pub. No.: WO2015/034247
PCT Pub. Date: Mar. 12, 2015

(65) Prior Publication Data
US 2016/0193174 A1    Jul. 7, 2016

(30) Foreign Application Priority Data
Sep. 3, 2013 (KR) .......... 10-2013-0105752

(51) Int. Cl.
*A61K 31/231* (2006.01)
*A61K 9/00* (2006.01)
*A61K 9/08* (2006.01)
*A61K 47/44* (2017.01)
*A61K 8/37* (2006.01)
*A61Q 19/00* (2006.01)
*A23L 33/10* (2016.01)

(52) U.S. Cl.
CPC ............ *A61K 31/231* (2013.01); *A23L 33/10* (2016.08); *A61K 8/37* (2013.01); *A61K 9/0014* (2013.01); *A61K 9/08* (2013.01); *A61K 47/44* (2013.01); *A61Q 19/00* (2013.01); *A23V 2002/00* (2013.01); *A61K 2800/10* (2013.01)

(58) Field of Classification Search
CPC .................................................. A61K 31/231
See application file for complete search history.

(56) References Cited

U.S. PATENT DOCUMENTS 7,662,853 B2 *  2/2010  Kim ........................ A61K 31/22
                                                      514/546

FOREIGN PATENT DOCUMENTS

| KR | 10-2000-0071887 A | 11/2000 |
| KR | 10-2005-0103259 A | 10/2005 |
| KR | 10-2006-0047447 A | 5/2006  |
| KR | 10-2007-0010841 A | 1/2007  |

OTHER PUBLICATIONS

Yang et al. Biol. Pharm. Bull, 2004, vol. 27, No. 7, pp. 1121-1125.*
M.-H. Kim, H.M. Chang, T.W. Kim, et al., "EC-18, a synthetic monoacetyldiacylglyceride, inhibits hematogenous metastasis of KIGB-5 biliary cancer cell in hamster model", J Korean Med Sci 2009; 24: 474-80, ISSN 1011-8934, DOI: 10.3346/jkms.2009.24.3.474.
PCT/ISA/237 issued in International Application No. PCT/KR2014/008229 issued Mar. 8, 2016.

* cited by examiner

*Primary Examiner* — James D Anderson
(74) *Attorney, Agent, or Firm* — Nath, Goldberg & Meyer; Joshua B. Goldberg; Tanya E. Harkins

(57) ABSTRACT

The present invention relates to a pharmaceutical composition, functional health food composition, quasi-drug composition, and cosmetic composition containing a monoacetyldiacylglycerol compound as an active ingredient for preventing, treating or improving atopic dermatitis. The monoacetyldiacylglycerol compound of the present invention has an excellent effect of suppression of IL-4 and IgE secretion, thereby overcoming side effects of an atopic dermatitis treatment agent currently in use, having no toxicity, and exhibiting an excellent treatment effect, and thus can be useful as a composition for preventing, treating, and ameliorating atopic dermatitis.

12 Claims, 7 Drawing Sheets

[FIG. 1]
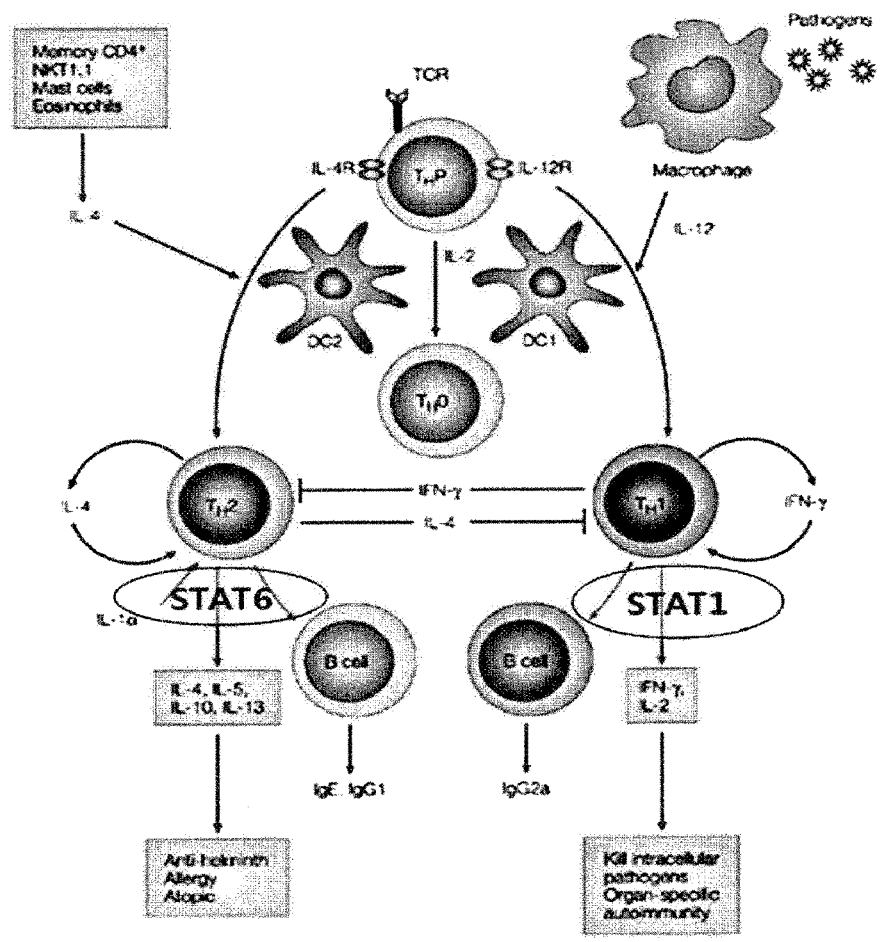
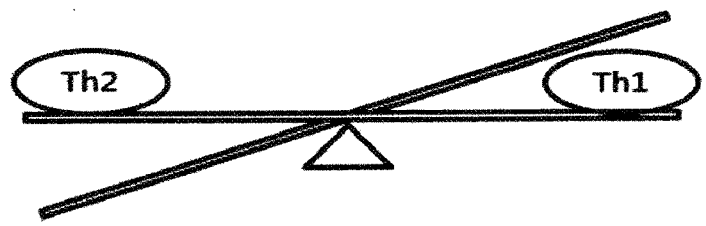

[FIG. 2]
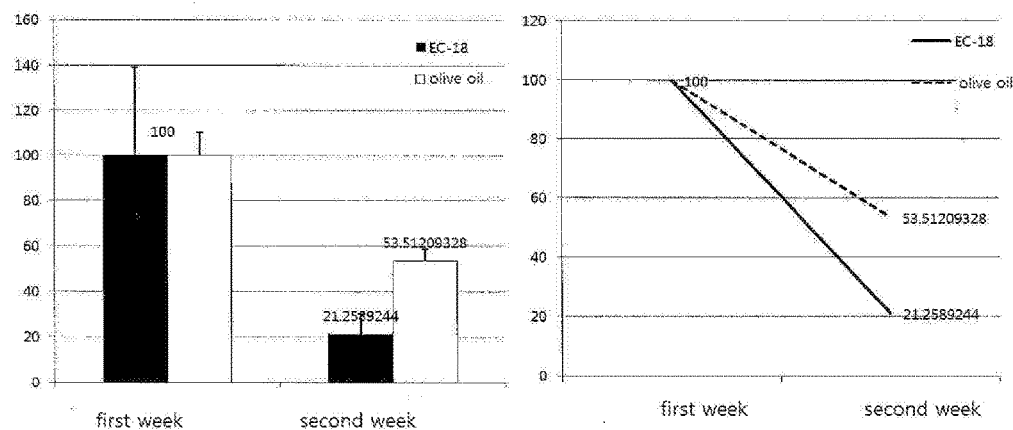
[FIG. 3]
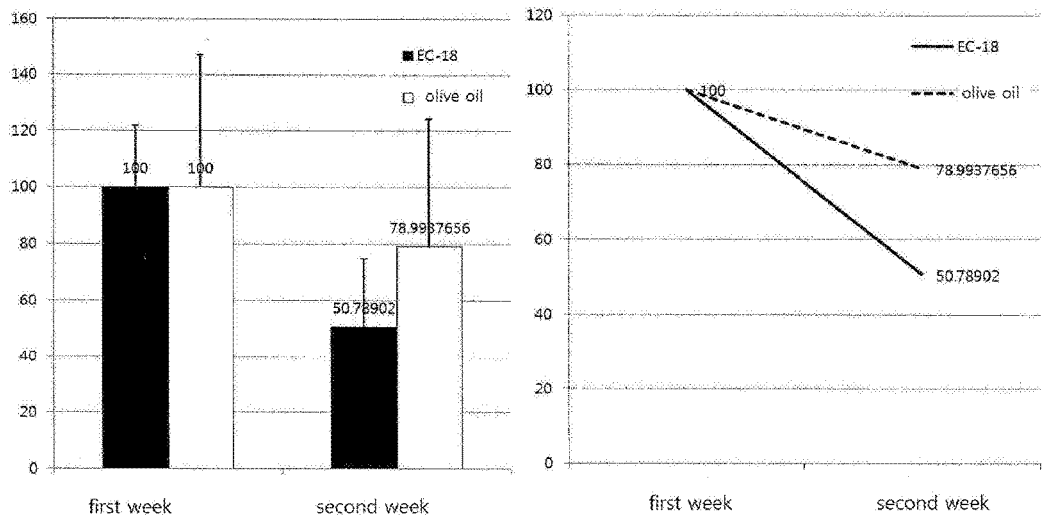

[FIG. 4]
A) Group treated with EC-18
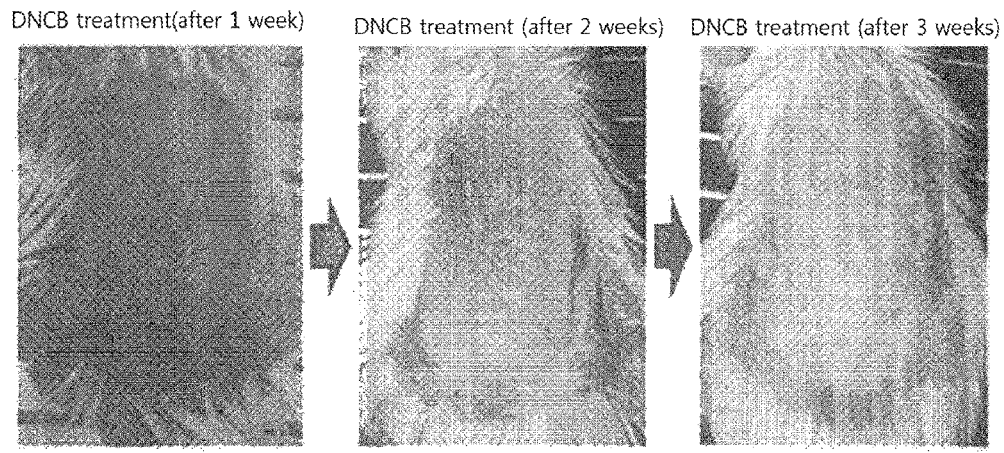
B) control group-olive
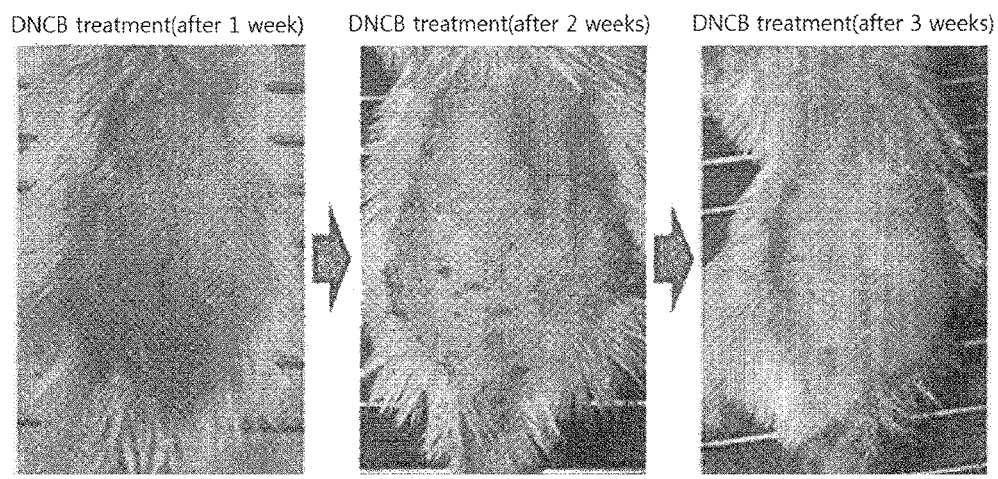

[FIG. 5]
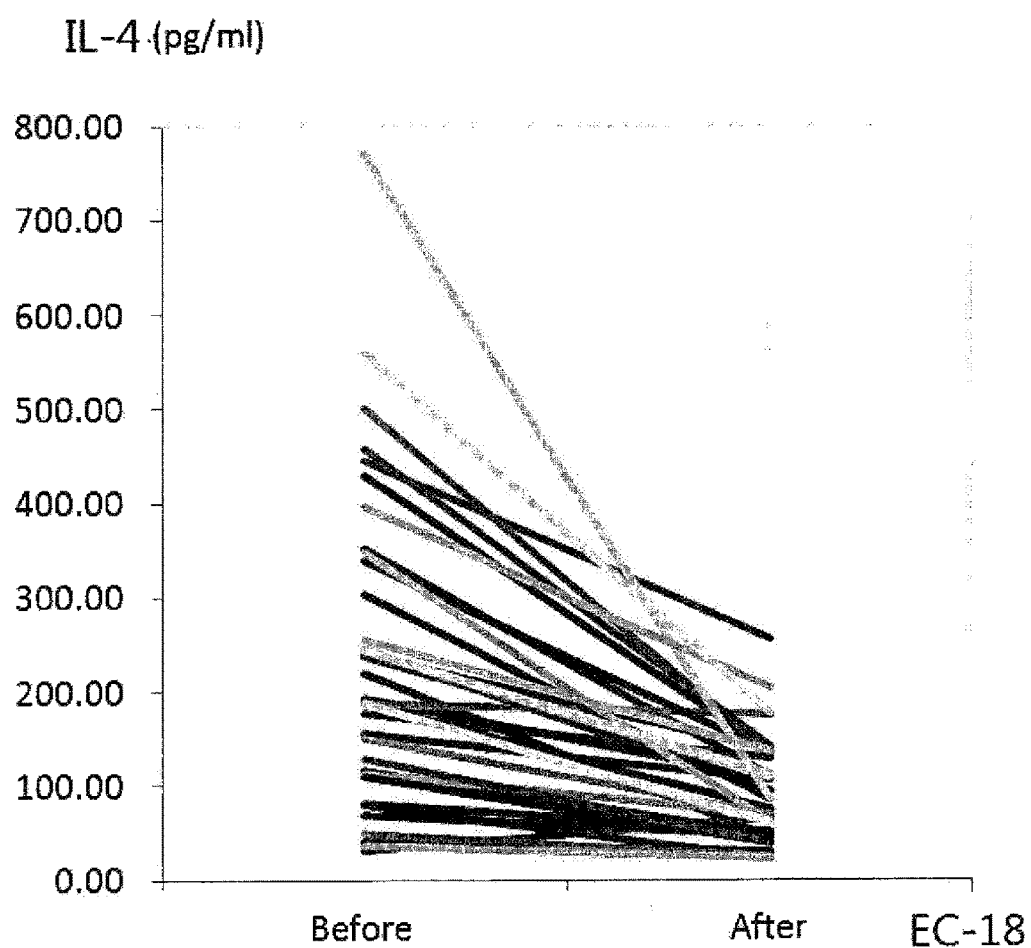

[FIG. 6]
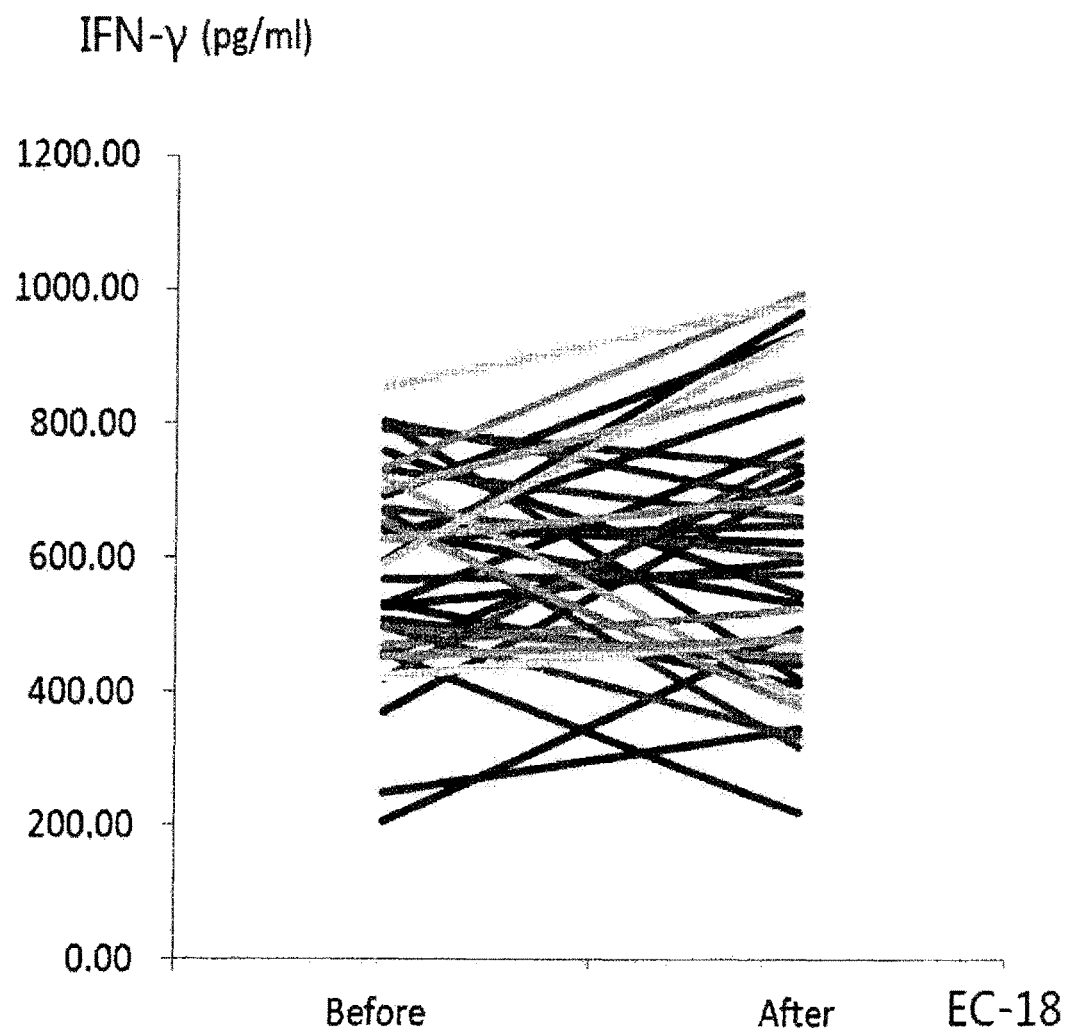

[FIG. 7]
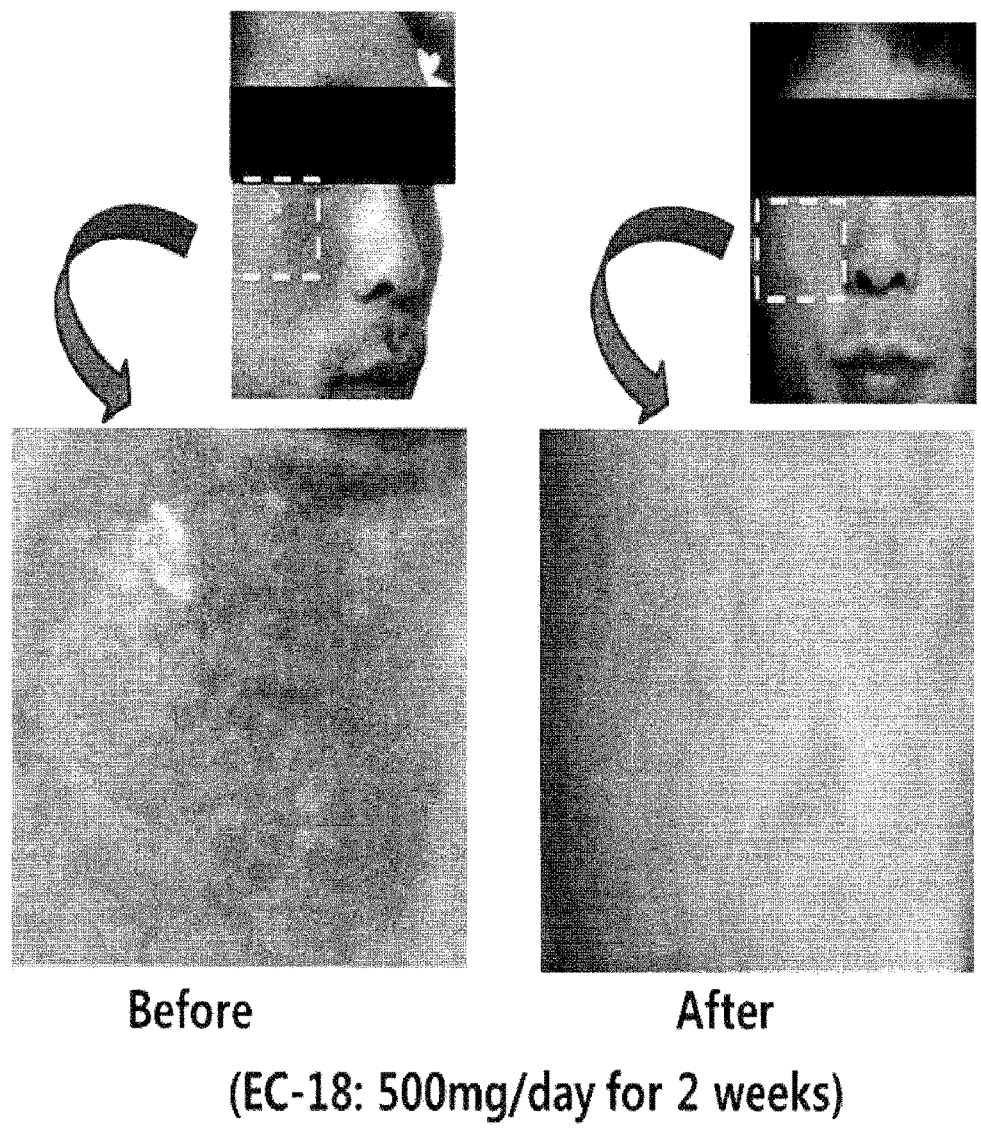

[FIG. 8]
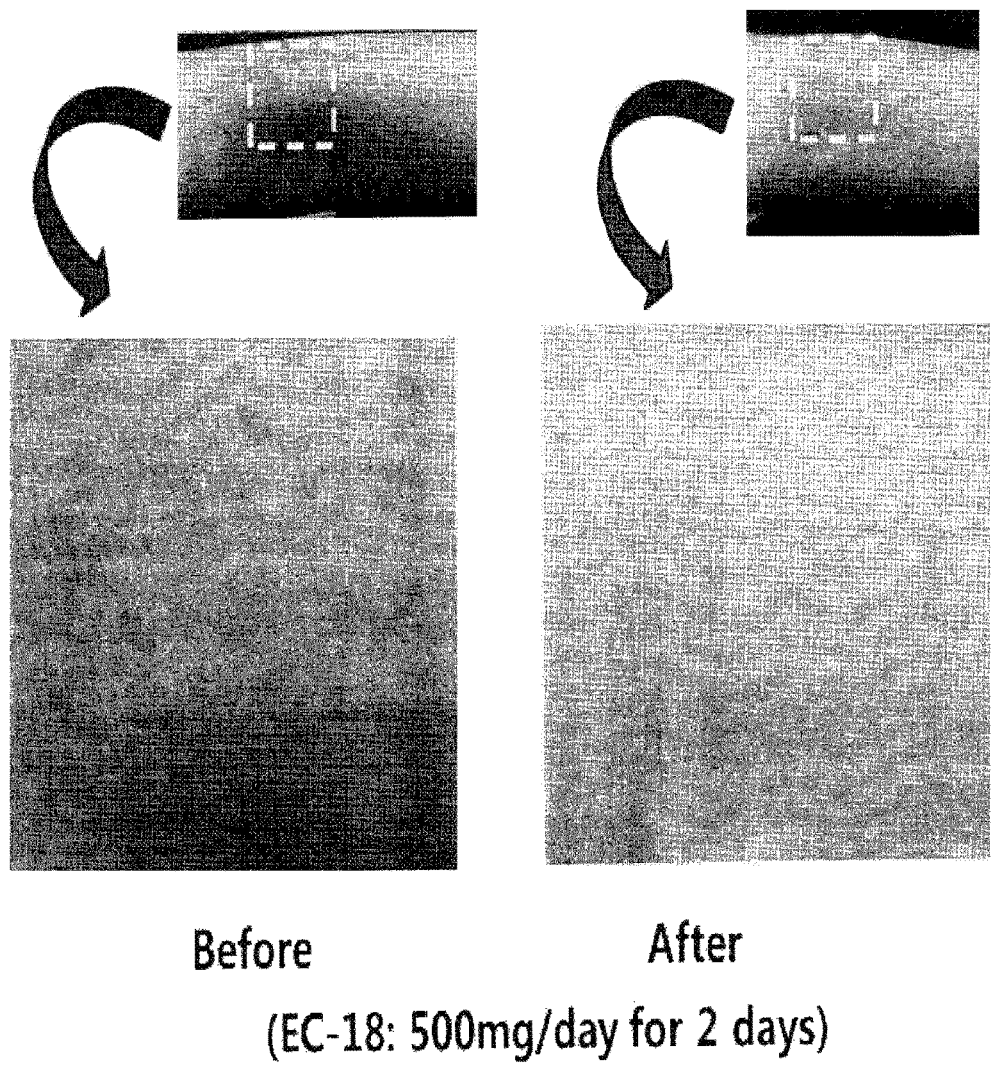
Before    After
(EC-18: 500mg/day for 2 days)

COMPOSITION CONTAINING MONOACETYLDIGLYCERIDE COMPOUND AS ACTIVE INGREDIENT FOR PREVENTING OR TREATING ATOPIC DERMATITIS

This is a National Phase Application filed under 35 U.S.C. 371 as a national stage of PCT/KR2014/008229, filed Sept. 3, 2014, an application claiming the benefit from Korean Application No. 10-2013-0105752, filed Sept. 3, 2013, the content of each of which is hereby incorporated by reference in its entirety.

TECHNICAL FIELD

The present invention relates to a pharmaceutical composition, functional health food composition, quasi-drug composition, and cosmetic composition containing a monoacetyldiacylglycerol compound as an active ingredient for preventing, treating or improving atopic dermatitis.

BACKGROUND ART

Atopic dermatitis, a chronic recurrent pruritic dermatitis, commonly occurs in infants and children groups and is a disease accompanied by pruritus, dry skin or eczema characteristic in patients and their families. Typical symptoms of atopic dermatitis appears in hand, scalp, face, neck, elbows, knees, etc.; the skin becomes very dry, the itching and inflammation appears on the skin, the skin is exfoliated like the scales and when the scratching in the skin is badly severe, phenomenon of lichenification making deep wrinkle in skin appears. The direct cause of the occurrence of atopic dermatitis has been not yet clearly revealed. Therefore, the studies for atopic dermatitis have been conducted continuously. In order to treat these atopic dermatitis, conventionally, there have been proposed materials including ceramides, linoleic acid, vegetable oil or mineral oil, steroid preparations such as hydrocortisone, and antibacterial and anti-inflammatory materials thereof. However, steroids may inhibit skin growth or cause side effects, thereby leading to adverse effects, and urea peroxide may lead to over-stimulation of the skin. Antibiotics such as the antihistamine etc. may potentially cause side effects of bacteria resistance and photosensitivity and when antibiotics are applied to the skin for a long time, there is a possibility to cause side effects of telangiectasia and/or the thickness increase or expansion of the stratum corneum. On the other hand, gamma-linolenic acid which is used a lot in recent for alleviating atopic dermatitis is easily oxidized. Thus, gamma-linoleic acid has not only a low stability but also a relatively strong skin irritating so that It is difficult to apply to sensitive skin.

EC-18, as a kind of monoacetyldiglyceride compounds, was separated or extracted from the natural deer antler. It is known that EC-18 increases survivability ratio of animals in sepsis animal model experiment using cecal-ligation-puncture, and shows no-toxicity in GLP (Good Laboratory Practice) toxicity test. However, the effect of monoacetyldiacylglycerol compounds including EC-18 is not known or disclosed in atopic dermatitis. Thus the present inventors aimed to find a compound derived from natural products or a novel compound for the prevention or treatment of atopic dermatitis and found that the monoacetyldiacylglycerol compound inhibits secretion of IL-4 and IgE and can be used to prevent or treat atopic dermatitis.

DISCLOSURE

Technical Problem

An object of the present invention is to provide a pharmaceutical composition, functional food composition, a cosmetic composition and a quasi-drug composition for preventing, treating or improving atopic dermatitis.

Another object of the present invention is to a method for preventing or treating atopic dermatitis comprising a step of administrating the pharmaceutical composition to a subject who has possibility of onset of atopic dermatitis or suffering from atopic dermatitis.

Technical Solution

In an example to achieve the these and other objects, the present invention provides a pharmaceutical composition containing a monoacetyldiacylglycerol compound represented by following Formula 1 as an active ingredient for preventing or treating atopic dermatitis.

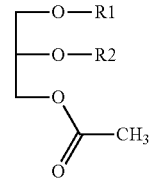

[Formula 1]

wherein R1 and R2 are independently a fatty acid group of 14 to 22 carbon atoms.

In detail, the pharmaceutical composition for preventing or treating atopic dermatitis according to the present invention includes a monoacetyldiacylglycerol compound represented by the Formula 1. In the present invention, the term "monoacetyl diacyl glycerol compound" means glycerol derivatives having one acetyl group and two acyl groups, and can be referred as "monoacetyl diacyl glycerol (MADG)".

In the monoacetyl diacyl glycerol compound of Formula 1, R1 and R2 are independently a fatty acid residue of 14 to 22 carbon atoms. Fatty acid residue refers to the acyl moiety resulting from formation of an ester bond by reaction of a fatty acid and an alcohol. Non-limiting examples of R1 and R2 thus include palmitoyl, oleoyl, linoleoyl, linolenoyl, stearoyl, myristoyl, arachidonoyl, and so on. Preferable combinations of R1 and R2 (R1/R2) include oleoyl/palmitoyl, palmitoyl/oleoyl, palmitoyl/linoleoyl, palmitoyl/linolenoyl, palmitoyl/arachidonoyl, palmitoyl/stearoyl, palmitoyl/palmitoyl, oleoyl/stearoyl, linoleoyl/palmitoyl, linoleoyl/stearoyl, stearoyl/linoleoyl, stearoyl/oleoyl, myristoyl/linoleoyl, myristoyl/oleoyl, and so on. In optical activity, the monoacetyl diacyl glycerol compound of Formula 1 can be (R)-form, (S)-form or a racemic mixture, and may include their stereoisomers.

In one embodiment, the monoacetyl diacyl glycerol compound is a compound of the following Formula 2.

[Formula 2]

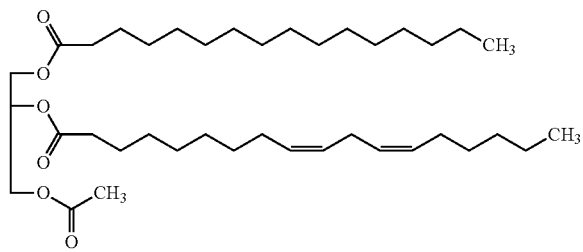

The compound of Formula 2 is 1-palmitoyl-2-linoleoyl-3-acetylglycerol, sometimes referred as "EC-18" in this specification. R1 and R2 of the compound of Formula 2 are palmitoyl and linoleoyl, respectively.

The monoacetyldiacylglycerol compounds can be separated and extracted from the natural deer antler or can be produced by known organic synthesis methods (Korean Registered Patents No. 10-0789323). More specifically, deer antler is extracted with hexane, followed by extracting the residue with chloroform and removing the chloroform to provide chloroform extracts. The volume of the solvents for this extraction is just enough to immerse the deer antler. In general, about 4-5 liters of hexane and/or chloroform for 1 kg of deer antler is used, but not limited thereto. The extracts obtained by this method is further fractionated and purified using series of silica gel column chromatograph and TLC method to obtain the monoacetyldiacylglycerol compound for the present invention. A solvent for the extraction is selected among chloroform/methanol, hexane/ethylacetate/acetic acid, but not limited thereto.

A chemical synthetic method for the preparation of monoacetyldiacylglycerol compounds is shown in Korean Registered Patents No. 10-0789323. Specifically, the method comprises (a) a step of preparing 1-R1-3- protecting group -glycerol by adding a protecting group in the position 3 of 1-R1-glycerol; (b) a step of preparing 1-R1-2-R2-3- protecting group -glycerol by introducing R2 in the position 2 of the 1-R1-3- protecting group -glycerol; and (c) a step of preparing the desired monoacetyldiacylglycerol compound by performing a deprotection reaction and the acetylation reaction of the 1-R1-3- protecting group -glycerol at the same time. The monoacetyldiacylglycerol compound may be further purified if necessary. Alternatively, monoacetyldiacylglycerol compounds can be prepared by acid decomposition of phosphatidylcholine (acetolysis) but is not limited thereto. Stereoisomers of the compounds of formula (I) are also within the scope of the invention.

In the present invention it is shown that monoacetyldiacylglycerol compounds are capable of reducing the secretion of IL-4 and IgE, and thus the monoacetyldiacylglycerol compounds can be effectively used for the prevention or treatment of atopic dermatitis.

In the present invention, the term "prevention" means any activities to suppress or delay onset of atopic dermatitis by the administration of the pharmaceutical composition of the present invention and "treatment" means any action to improve symptoms caused by atopic dermatitis or to change symptoms by atopic dermatitis to more beneficial states. In the present invention, the term "atopic dermatitis" is a chronic recurrent inflammatory skin disease and refers to a disease accompanied by pruritus (itching), dry skin and eczema characteristic. In acute lesions of atopic dermatitis, a significant increase in the serum immunoglobulin E (IgE) appears as a feature of atopic dermatitis. In addition thereto, subjected to the sensory evaluation of the pathological changes of the tissue lesion and dermatitis lesion, the diagnosis and severity of atopic dermatitis are determined. Although the exact cause of atopic dermatitis has not been yet fully understood, it has been reported that immunological, non-immunological mechanisms with genetic predisposition are involved in atopic dermatitis. Extrinsic atopic dermatitis, the majority of atopic dermatitis, is caused by immune mechanisms associated with IgE. There are many reports that delayed immune response due to abnormal T cell rather than immediate-type immune response to a specific allergen is involved in extrinsic atopic dermatitis. Also, recently, it had been reported that Th2-related cytokines such as IL-4 which induces the production of IgE from B cells is the cause of atopy (J S Kang et al., Inhibition of atopic dermatitis by topical application of silymarin in NC/Nga mice. Int. Immunopharm. (2008) 8:1475-1480).

FIG. 1 is a schematic view for explaining the cause of atopy. FIG. 1 shows that Th1 ($T_H1$) and Th2 ($T_H2$) cells play a crucial role in maintaining balance in the immune response and when Th1 and Th2 expression loses its balance, the atopy can occur.

The examples of the present invention confirmed that of atopic dermatitis model animals induced through the application of the DNCB (1-Chloro-2,4-dinitro-benzene) compound, the experimental groups treated with the EC-18, compared to the untreated group (olive oil treatment group), showed that IL-4 and IgE levels was significantly decreased (Example 1 and 2). This shows that the monoacetyldiacylglycerol compounds is effective in the treatment of atopic dermatitis.

The pharmaceutical composition containing monoacetyldiacylglycerol compounds of the present invention may additionally include conventional pharmaceutically acceptable carriers, excipients, or diluents. The amount of monoacetyldiacylglycerol compounds in the pharmaceutical composition can be widely varied without specific limitation, and is specifically 0.0001 to 100.0 weight %, preferably 0.001 to 50 weight %, more preferably 0.01 to 20 weight % with respect to the total amount of the composition.

The pharmaceutical composition may be formulated into various forms for oral or non-oral administration, for example one selected from a group consisting of tablet, bolus, powder, granule, capsule such as hard or soft gelatin capsule, emulsion, suspension, syrup, emulsifiable concentrate, sterilized aqueous solution, non-aqueous solution, freeze-dried formulation, suppository, and so on. In formulating the composition, conventional excipients or diluents such as filler, bulking agent, binder, wetting agent, disintegrating agent, and surfactant can be used. The solid formulation for oral administration includes tablet, bolus, powder, granule, capsule and so on, and the solid formulation can be prepared by mixing one or more of the active components and at least one excipient such as starch, calcium carbonate, sucrose, lactose, gelatin, and so on. Besides the excipient, a lubricant such as Magnesium stearate and talc can also be used. The liquid formulation for oral administration includes emulsion, suspension, syrup, and so on, and may include conventional diluents such as water and liquid paraffin or may include various such as wetting agent, sweeting agent, flavoring agent, and preserving agent. The formulation for non-oral administration includes sterilized aqueous solution, non-aqueous solution, freeze-dried formulation, suppository, and so on, and solvent for such solution may include propylene glycol, polyethylene glycol, vegetable oil such as olive oil, and ester for syringe injection such as ethyl oleate.

Base materials of the suppository may include witepsol, macrogol, tween 61, cacao butter, Laurin and glycerogelatine.

The composition of the present invention can be administered in a pharmaceutically effective amount. The term "pharmaceutically effective amount" is used to refer to an amount which is sufficient to achieve a desired result in a medical treatment. The "pharmaceutically effective amount" can be determined in accordance with type, age and sex of a subject, severity and type of disease, activity of drug, sensitivity to drug, administration time, period and route, excretion rate, and other well known criteria in medical field. The composition of the present invention can be administered alone or with other medicines sequentially or simultaneously, or administered once or several times. Considering all the above factors, it is important to dose the amount that can achieve the maximum effect with the minimum amount with no side effects, which can be readily determined by those skilled in the art. The preferable amount of the composition of the present invention can be varied in accordance with the condition and weight of patient, severity of disease, formulation type of drug, administration route and period of drug. Appropriate total amount of administration per 1 day can be determined by a doctor of related medical filed, and generally 0.001 to 1000 mg/kg, preferably 0.05 to 200 mg/kg, more preferably 0.1 to 100 mg/kg once or several times by dividing in 1 day. The composition of the present invention can be administered to any subject which requires the suppression of blood cancer or cancer metastasis. For example, the composition of the present invention can be administered to not only human but also non-human animal (specifically mammals) such as monkey, dog, cat, rabbit, guinea pig, rat, mouse, cow, sheep, pig, goat, and so on. The composition of the present invention can be administered by conventional various methods, for example, by oral or rectum administration, or by intravenous, intramuscular, subcutaneous or cerebrovascular injection.

As other aspect of the present invention, the present invention provides a health functional food for preventing or improving atopic dermatitis comprising monoacetyldiacylglycerol derivatives of Formula 1 as active component(s),

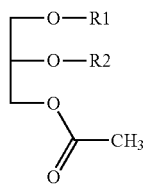

[Formula 1]

wherein R1 and R2 are independently a fatty acid group of 14 to 22 carbon atoms, but are not limited thereto.

For preventing or improving atopic dermatitis, the monoacetyldiacylglycerol derivatives of the present invention can be included in the health functional food. The monoacetyldiacylglycerol compounds, atopic dermatitis are previously explained in detail. The term "improving" means every change which reduces or advantageously changes the symptoms in a subject having or suspicious of having atopic dermatitis.

When the composition of the present invention is included in the health functional food, the composition can be included alone or with other active component. The amount of the compounds of the present invention in the health functional food can be determined in accordance with the intended use of the health functional food. Generally, when preparing health functional food or beverage, the composition of the present invention can be included in the amount of less than 15 weight part, preferably less than 10 weight part. In case of long term administration for maintaining one's health, the amount of the composition can be reduced. However, since the active component does not cause any adverse effect, the amount of the composition can be increased by more than the above mentioned amount. The health functional food including the composition of the present invention can be any conventional food or beverage. Specific examples of the food include meat, sausage, bread, chocolate, candy, snack, biscuit, pizza, Ramen, noodles, gum, ice cream, dairy product, soup, beverage, tea, drink, alcoholic drink, vitamin complex, and so on. If necessary, the food of the present invention can also include food for an animal.

When the health functional food is beverage, the beverage may include conventional sweetener, flavoring agent, natural carbohydrate, and so on. Examples of the natural carbohydrate include monosaccharide such as glucose and fructose, disaccharide such as maltose and sucrose, polysaccharide such as dextrin and cyclodextrin, and sugar alcohol such as xylitol, sorbitol, and erythritol. The preferable amount of the natural carbohydrate can be about 0.01 to 0.04 g, more preferably about 0.02 to 0.03 g with respect to 100 ml of the beverage of the present invention. Examples of the sweetener includes natural sweeteners such as Thaumatin and Stevia extract and artificial sweeteners such as saccharin and aspartame. The health functional food of the present invention may further include various nutritional supplement, vitamin, electrolyte, flavoring agent, coloring agent, pectic acid and its salt, alginic acid and its salt, organic acid, protective colloid, thickener, pH adjuster, stabilizer, preservative, glycerin, alcohol, juice and so on.

As other aspect of the present invention, the present invention provides quasi-drug compositions for preventing or improving atopic dermatitis comprising monoacetyldiacylglycerol derivatives of Formula 1 as active component(s),

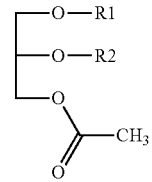

[Formula 1]

wherein R1 and R2 are independently a fatty acid group of 14 to 22 carbon atoms, but are not limited thereto.

For preventing or improving atopic dermatitis, the monoacetyldiacylglycerol derivatives of the present invention can be included in the quasi-drug compositions. The monoacetyldiacylglycerol compounds, atopic dermatitis are previously explained in detail.

The term "quasi-drug" means a product which falls under any of the followings: (a) Fibers, rubber products or similar products used for the purpose of treating, alleviating, or preventing human or animal diseases; (b) Non-appliance, non-machinery or similar products which have insignificant influences on or do not directly act upon human bodies; and (c) Preparations used for sterilization, insecticide and purposes similar thereto in order to prevent communicable diseases. However, the term "quasi-drug" does not include (a) products used for the purposes of diagnosis, medical care, alleviation, treatment or prevention of diseases of human beings or animals, excluding appliances, machinery and equipment; or (b) products, other than appliances, machinery or equipment, used for the purpose of exerting pharmacological effects upon the structure or functions of human beings or animals. Quasi-drugs include the external preparations for skin and personal care products. The quasi-drug composition of the present invention for preventing or improving atopic dermatitis may consist of only or substantially pure monoacetyldiacylglycerols, or may include the monoacetyldiacylglycerol and other conventional ingredients of quasi-drugs. The amount of monoacetyldiacylglycerol in the quasi-drug composition can be determined suitably in accordance with the intended use. The skin external preparations to which the compound of the present invention can be added include, for example, ointments, lotions, spray agents, patches, creams, powders, suspensions, and gels but are not limited thereto.

As other aspect of the present invention, the present invention provides cosmetic compositions for preventing or improving atopic dermatitis comprising monoacetyldiacylglycerol derivatives of Formula 1 as active component(s),

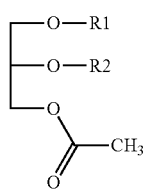

[Formula 1]

wherein R1 and R2 are independently a fatty acid group of 14 to 22 carbon atoms, but are not limited thereto.

For preventing or improving atopic dermatitis, the monoacetyldiacylglycerol derivatives of the present invention can be included in the cosmetic compositions. The monoacetyldiacylglycerol compounds, atopic dermatitis are previously explained in detail. The cosmetic compositions for preventing or improving atopic dermatitis include monoacetyldiacylglycerol compounds of 0.001 to 50% by weight, more preferably 0.01 to 20% by weight, most preferably 0.1 to 10% by weight, with respect to the total composition weight, but is not limited thereto.

In addition, the cosmetic composition of the present invention may include, without limitation, the components typically allowed in addition to the active ingredient, for example, conventional adjuvants such as antioxidants, stabilizers, solubilizers, vitamins, pigments and perfumes, and carriers.

The cosmetic compositions of the present invention may be formulated into various forms, for examples solution, topical ointments, creams, foams, nutrition lotion, softening longevity, pack, yuyeonsu, lotion, makeup base, essence, soap, liquid cleaning fee and bath, sunscreen cream, sunoil, suspensions, emulsions, pastes, gels, lotions, powders, soaps, surfactant-containing cleansing, oil, powder foundation, emulsion foundation, wax foundation, patch and spray, but not limited thereto. In addition, the cosmetic composition of the present invention may include one or more cosmetically acceptable carrier which is formulated with the general chemical skin cosmetic composition additionally, for example oil, water, surfactants, humectants, lower alcohols, thickeners, chelating agents, dyes, preservatives, fragrances, but is not limited thereto.

Cosmetic chemically acceptable carrier contained in the cosmetic composition of the present invention varies with the formulation thereof.

If the formulation is an ointment, paste, cream or gel, as a carrier component, animal oils, vegetable oils, waxes, paraffins, starch, tragacanth, cellulose derivatives, polyethylene glycols, silicones, bentonites, silica, talc, zinc oxide or a mixture thereof may be used. If the formulation is powder or spray, as a carrier component, lactose, talc, silica, aluminum hydroxide, calcium chamber Kate, polyamide powder, or mixtures thereof can be used. In particular in the case of a spray formulation, a propellant such as chlorofluorocarbon, propane/butane or dimethyl ether can be additionally included. When the formulation is a solution or emulsion, a solvent, a solubilizer or emulsifying agent is used as the carrier component, for example, water, ethanol, isopropanol, ethyl carbonate, ethyl acetate, benzyl alcohol, benzyl benzoate, propylene glycol, 1, 3- and butyl glycol oil can be used. In particular, cottonseed oil, peanut oil, corn rapeseed oil, olive oil, castor oil and sesame oil, glycerol aliphatic ester, polyethylene fatty acid ester or glycol sorbitan fatty acid ester can be used. In the case of the formulation of a suspension, as carrier components, liquid diluents such as water, ethanol or propylene glycol, ethoxylated isostearyl alcohols, suspending agents such as polyoxyethylene sorbitol esters and polyoxyethylene sorbitan esters, microcrystalline cellulose, aluminum meta-hydroxide, bentonite, agar or tragacanth, etc. may be used. In case of the formulation of soap, as a carrier component, alkali metal salts of fatty acids, fatty acid hemi-ester salt, fatty acid protein hydrolysates, isethionates, lanolin derivatives, fatty alcohol, vegetable oil, glycerol, sugar and the like may be used. If the formulations of the present invention is surface-active agent-containing cleansing, as a carrier component, aliphatic alcohol sulfate, aliphatic alcohol ether sulfate, sulfosuccinate monoester, isethionate, imidazolinium derivatives, methyl taurates, sarcositate, fatty acid amide ether sulfate, alkyl amido betaine, aliphatic alcohol, fatty acid glyceride, fatty acid diethanolamide, vegetable oils, lanolin derivatives, or ethoxylated glycerol fatty acid esters, and the like may be used.

As another aspect of the present invention, the present invention provides a method for preventing or treating atopic dermatitis comprising a step of administering the pharmaceutical composition to a subject who is suspicious of having atopic dermatitis.

The "subject who is suspicious of having atopic dermatitis" includes not only an animal including human being which has atopic dermatitis but also potentially has atopic dermatitis. The subject who is suspicious of atopic dermatitis can be effectively treated by administering the pharmaceutical composition containing the composition or the pharmaceutically acceptable salt thereof of the present invention. atopic dermatitis are previously explained in detail. The term "administering" means introducing the pharmaceutical composition of the present invention into the subject who is suspicious of having atopic dermatitis by any means. The administration route can be any route such as oral or non-oral route. More specifically, it can be administered in a transdermal mode of administration through the topical application etc., but not limited thereto.

The method for treating blood cancer comprises a step of administering an effective amount of a pharmaceutical composition comprising the monoacetyldiacylglycerol compounds of formula I to a patient in need thereof. An appropriate total amount of administration per 1 day can be determined by a physician, and is generally about 0.001 to about 1000 mg/kg, preferably, about 0.05 to 200 mg/kg, more preferably about 0.1 to about 100 mg/kg. The total administration amount per day can be administered once a day or can be administered in divided doses multiple times daily. However, the specific therapeutically effective amount of the monoacetyldiacylglycerol administered to a particular patient can be varied depending on the type and degree of the response to be achieved in the treatment, the specific composition, including whether another agent is included in the composition, the patient's age, body weight, general health status, sex, diet, administration time, administration route, the ratio of composition, treatment period, other drugs used together in the treatment and a variety of factors well known in the medical field.

Effect of Invention

Monoacetyldiacylglycerol compounds of the invention are excellent in the effect of inhibiting the expression of IL-4 and IgE, thereby overcoming side-effects of currently used remedy for atopic dermatitis, while having no toxicity and excellent treatment effect so that Monoacetyldiacylglycerol compounds can be usefully used for the prevention, treatment and improvement of atopic dermatitis.

BRIEF DESCRIPTION OF THE DRAWINGS

FIG. 1 is a schematic view for explaining the causes of atopic.

FIG. 2 is a diagram showing the expression level of IL-4 for up to two weeks after treatment of EC-18 in mice.

FIG. 3 is a diagram showing the expression level of IgE for up to two weeks after treatment of EC-18 in mice.

FIG. 4 is a photograph showing the degree of atopic disease for 3 weeks in mice of the EC-18 administration group and the mice of olive oil administration group (control group).

FIG. 5 is a graph showing the expression level of Th2 cytokine (IL-4) when EC-18 was administrated to normal subjects for 4 weeks.

FIG. 6 is a graph showing the expression level of Th1 cytokine (IFN-γ) when EC-18 was administrated to normal subjects for 4 weeks.

FIG. 7 is a photograph of the atopic symptoms change after EC-18 was administrated to a patient having strong atopic symptom.

FIG. 8 is a photograph of the atopic symptoms change after EC-18 was administrated to a patient having weak atopic symptom.

DETAILED DESCRIPTION OF THE INVENTION

A more detailed description of the invention will be made by reference to the attached drawings, which are intended for better understanding of the present invention and will not limit the present invention. Hereinafter, unless otherwise noted, ratios and percentages are by weight.

EXAMPLE

Induction of Atopic Dermatitis by DNCB Application

DNCB (1-Chloro-2,4-dinitrobenzene, Sigma Aldrich) was diluted to 0.2% by the solvent in which olive oil and acetone were mixed in a ratio of 1:4. Diluted DNCB was applied onto back of each 7-week-old Balb/c mouse whose hairs on back were removed. During the first week application was made seven times continuously, and from the second week, application was made every two days to induce atopy.

Experimental Example 1

Inhibition Effect of IL-4 Expression by EC-18

A mixture of EC-18 and olive oil was orally administrated to the mouse 7 times during the first week by 100 µl each time in dose of 2 mq/rat, and after then, for 11 times, was administered orally by 100 µl each time in dose of 1 mg/rat, that is the mixture was orally administrated totally 18 times. For the measurement of IL-4, blood was collected from veins under the eyes of mice treated, through ocular blood (Eye bleeding) method. Before administration, one week after the administration, 2 weeks after administration, 3 weeks after administration, a total of four times, blood samples were collected using a Pasteur pipette (Pasteur pipet, Hilgenberg). After collecting the blood of about 350 µl in the EP tube, the blood was centrifuged to separate only serum and IL-4 present in the serum was analyzed by ELISA (enzyme-linked immunosorbent assay) method. Mouse IL-4 capture antibody (BD bioscience) was diluted with 1×PBS to 2 µg/ml, dispensed to each of 96-well plate (Thermo) for mouse L-4 ELISA by 200 µl, and then coated overnight and washed by a wash buffer in which 0.05% tween 20 was diluted in 1×PBS. After washing three times, 1% BSA was dispensed to each well by 200 µl and blocking buffer was placed for 1 hour at room temperature (RT), and washing was performed three times under the same conditions. Thereafter, the serum obtained from the mice was dispensed to each well by 100 µl, and the wells were placed for reaction at room temperature for 2 hours after dispensing, and then washed five times under the same conditions. After washing, detection antibody (1:500) conjugated-HRP (1:250) diluted with 1% BSA was dispensed to each well by 100 µl and then was placed for reaction at room temperature for 1 hour. After seven-times-washing, a substrate solution of 100 µl was dispensed to each well, and the color development was observed in a state where light is blocked. When the color development is completed, the stop solution (2N $H_2SO_4$+ DW) was dispensed by 100 µl, and the amount of color development at 450 nm wavelength was measured at ELISA Reader. As a result, comparing the levels of IL-4 (the average of the measured value 4 times) in one week after the administration and two weeks after the administration, the IL-4 level was reduced by approximately 50% v in the control group administered with olive oil, on the other hand, the IL-4 level was reduced by 80% in the test group the administration of EC-18. That is, it was confirmed that IL-4 produced by the atopic induction was rapidly reduced by administration of EC-18 (FIG. 2).

Experimental Example 2

IgE Expression Inhibitory Effect by EC-18

Using the serum separated from the mouse blood, was measured the expression levels of IgE in the ELISA method as shown in Experimental Example 1. In IgE ELISA for the mouse, IgE capture antibody (BD bioscience) was diluted with 1×PBS to 2 µg/ml, dispensed to each of 96-well plate (Thermo) by 200 µl, coated for 12 hours, washed using a wash buffer in which 0.05% tween 20 was diluted in 1×PBS.

After washing three times, 1% BSA was dispensed to each well by 200 µl and blocking buffer was placed for 1 hour at room temperature (RT) conditions, and then final washing was performed. Thereafter, the serum obtained from the mice was dispensed to each well by 100 µl, and the wells were placed for reaction at room temperature for 1 hours after dispensing, and unreacted IgE is washed under the same conditions. After washing, detection antibody (BD bioscience) was diluted with 1% BSA to be 2 µg/ml and dispensed to each well by 100 µl and then was placed for reaction at room temperature for 1 hour. After six-times-washing, Streptoavidin-HRP (Thermo) was mixed in 1% BSA in a ratio of 1:10,000 to be dispensed by 100 µl to add the substrate to the reacting IgE. After incubation for 30 minutes at room temperature, washing was performed 6 times, a substrate solution was dispensed to each well, and the color development was observed in a state where light is blocked. When the color development is completed, the stop solution (2N $H_2SO_4$+DW) was dispensed by 50 µl, and the amount of color development at 450 nm wavelength was measured. As a result, comparing the levels of IgE in one week after the administration and two weeks after the administration, in the control group administered with only olive oil, the IgE level was reduced by approximately 22%, on the other hand, in the test group the administration of EC-18, the IgE level was reduced by about 50% (FIG. 3).

Experimental Example 3

Visual Inspection on Improvement Effect of Atopic by EC-18

Atopic disease models commonly used in the laboratory is a technique that induces contact Hypersensitivity (CHS) by sensitization to DNCB (1-Chloro-2,4-dinitro-benzene). This technique is a technique of inducing atopic by diluting DNCB with a solvent in which acetone and olive oil are mixed in a ratio of 4:1 to be 0.2%, and then smearing the diluted on the skin, and is for the experiment for adjusting and maintaining the expression time so that artificially severe atopy-like appearance appears could be observed two weeks after the smearing. The degree of atopic disease was evaluated by dividing the state of erythema/emorrhage, scarring/dryness, edema), excoriation/erosion which are induced on the skin, respectively into three steps (0=null, 1=mild, 2=moderate, 3=severe) and then assigning the score up to 12 from zero. It was induced in the experimental group and the control group that the time when severe atopic status ((visual inspection index of 10) is reached was two weeks after the smearing of DNCB. Further, in order to maintain this condition, after two weeks, DNCB smearing was performed every two days.

FIG. 4 is a photograph showing the degree of atopic disease for 3 weeks in mice of the EC-18 administration group (test group) and the mice of olive oil administration group (control group). As shown in FIG. 4, in the control group administered with olive oil, visual inspection index was changed to 3 points after one week, 10 points after two weeks and 6 points after three weeks. In contrast, in the test group the administration of EC-18, visual inspection index was changed to 1 point after one week, 8 points after two weeks and 3 points after three weeks. This proves the therapeutic efficacy on the lesions of atopic dermatitis is also superior in a group of administration of EC-18. That is, after two weeks, when the visual inspection index in the control group was 10, the visual inspection index in the test group (EC-18 administration group) stayed in 8, which indicates that the EC-18 inhibits the production of atopic. In addition, from the visual inspection index after three weeks, the test group (EC-18 continuously-fed group) showed rapid atopic treatment and recovery than the control group (In test group the visual inspection index was reduced from 8 to 3, and in the control group the visual inspection index was reduced from 10 to 6).

Experimental Example 4

IL-4 and IFN-γ Expression after EC-18 Administration

EC-18 was administered to the normal healthy people (36 people) four weeks. EC-18 Lymphocytes separated from the blood before administration and after administration were incubated with ConA (concanavalin A). In order to measure the cytokine (IFN-γ and IL-4) which is separated from the lymphocyte (T cell) activated by Con A, culture medium was incubated for 42 hours, and were stored frozen. Purified antibody (capture antibody) of cytokine to be measured was dispensed to well (Nunc-immuno module, polysorp) by 0.2 µg/well, and left overnight at 4° C. to coat antigen. After well washing, blocking buffer (1% bovine serum albumin) treatment was performed for about 1 hour to inhibit the nonspecific binding. After washing the well, a cell culture solution was placed into each well and the antibody was combined with coating antigen for 2 hours. Antibody to which a peroxidase or biotin is bound was added, and the well was left at room temperature for 1 hour and thereafter washed. TMB (3,3',5,5'-Tetramethyl benzidine) substrate was directly added to antibody to which peroxidase is bound, and SAv-HRP (Streptavidin-Horseradish Peroxidase) was added to antibody to which biotin is bound, to react for 30 minutes, and then washed and TMB substrate was added. After approximately 10-30 minutes, stop solution was added into the well and absorbance at 450-570 nm was measured with Automatic Microplate reader (Molecular Devices, CA, USA). In the same manner, absorbance according to cytokine solution concentration was measured to plot standard curve, and the amount of cytokine contained in the sample was calculated by substituting the absorbance of the sample group. The change amount of cytokine calculated in this manner and significance ($P<0.05$) were shown in flowing Table 1 and FIGS. 5-6.

FIG. 5 is a graph showing the expression level of Th2 cytokine (IL-4) when EC-18 was administered to normal subjects for 4 weeks. As shown in FIG. 5, EC-18 administration to normal subjects for 4 weeks reduced the expression levels of Th2 cytokine (IL-4). FIG. 6 is a graph showing the expression level of Th1 cytokine (IFN-γ) when EC-18 was administered to normal subjects for 4 weeks. As shown in FIG. 6, even though EC-18 was administered to normal subjects for 4 weeks, the change did not occur uniformly in expression levels of cytokine Th1 (IFN-γ).

TABLE 1

|  | Before EC-18 administration (N = 36) | After EC-18 administration (N = 36) | P-value |
| --- | --- | --- | --- |
| IL-4 (pg/mL) | 246.6 ± 186.9 | 96.1 ± 64.2 | <0.001 |
| IFN-γ (pg/mL) | 686.4 ± 162.2 | 611.9 ± 209.7 | 0.473 |

Experimental Example 5

Observation of Atopic Symptom Alleviation in Patients with Atopic

To patients with severe atopic symptoms, the EC-18 was administrated every day at a dose of 500 mg/day for 2 weeks and atopic symptoms change which was taken were shown in FIG. 7. To a patient having a mild skin rash, the EC-18 was administrated every day at a dose of 500 mg/day for 2 days and atopic symptoms change which was taken were shown in FIG. 8. It was confirmed that as shown in FIGS. 7 and 8, when the EC-1 was administered to patients with atopic, the atopic symptoms are relaxed.

From the above description, a person skilled in the art will appreciate that the invention may be embodied in other specific forms without changing the technical spirit or essential characteristics. In this regard, the examples described above are intended to be illustrative in all respects and it should be understood as not limiting. The scope of the invention should be understood to include all ranges of the above detailed description and the appended claims, rather than the ranges of the specific examples, as well as all such modifications derived from those equivalents.

INDUSTRIAL APPLICABILITY

Monoacetyldiacylglycerol compound of the present invention can be used for the preparation of a pharmaceutical composition, functional health food composition, quasi-drug composition, and cosmetic composition for preventing, treating or improving atopic dermatitis.

The invention claimed is:

1. A method of treating atopic dermatitis, comprising: administering to a patient in need thereof a composition comprising a monoacetyldiacylglycerol compound of Formula 1 as an active ingredient, Formula 1 being

[Formula 1]

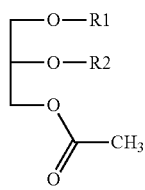

wherein R1 and R2 are independently a fatty acid group of 14 to 20 carbon atoms.

2. The method according to claim 1, wherein R1 and R2 are independently selected from the group consisting of palmitoyl, oleoyl, linoleoyl, linolenoyl, stearoyl, myristoyl, and arachidonoyl.

3. The method according to claim 1, wherein R1 and R2(R1/R2) is selected from the group consisting of oleoyl/pahnitoyl, palmitoyl/oleoyl, palmitoyl/linoleoyl, palmitoyl/linolenoyl, pahnitoyl/arachidonoyl, palmitoyl/stearoyl, palmitoyl/paimitoyl, oleoyl/stearoyl, linoleoyl/palmitoyl, linoleoyl/stearoyl, stearoyl/linoleoyl, stearoyl/oleoyl, myristoyl/linoleoyl, myristoyl/oleoyl.

4. The method according to claim 1, wherein the monoacetyldiacylglycerol compound is a compound of Formula 2:

[Formula 2]

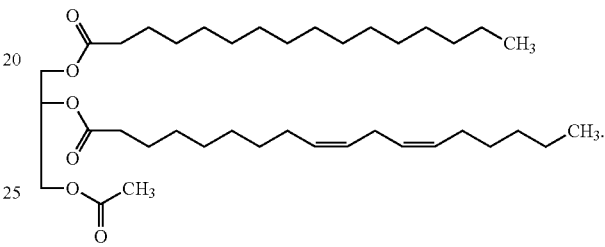

5. The method according to claim 1, wherein the monoacetyldiacylglycerol compound of Formula 1 is separated and extracted from natural deer antler.

6. The method according to claim 1, wherein the administration of the monoacetyldiacylglycerol compound reduces the secretion of IL-4 in the patient.

7. The method according to claim 1, wherein the administration of the monoacetyldiacylglycerol compound reduces the secretion of IgE in the patient.

8. The method according to claim 1, wherein the monoacetyldiacylglycerol compound of Formula 1 is present in the composition in an amount of 0.001 to 50% by weight of the composition.

9. The method according to claim 1, wherein the composition is in the form of a health functional food composition.

10. The method according to claim 1 wherein the composition is in the form of a quasi-drug composition.

11. The method according to claim 1, wherein the composition is in the form of a cosmetic composition.

12. The method according to claim 1, wherein the patient is a non-human patient.

* * * * *